US011446349B2

(12) United States Patent
Kim et al.

(10) Patent No.: US 11,446,349 B2
(45) Date of Patent: Sep. 20, 2022

(54) COMPOSITION FOR PREVENTING OR TREATING STROKE OR NEURODEGENERATIVE DISEASE, COMPRISING EXTRACT COMPLEX OF PUERARIA LOBATA AND SCUTELLARIA BAICALENSIS AS ACTIVE INGREDIENT

(71) Applicant: UNIVERSITY-INDUSTRY COOPERATION GROUP OF KYUNG HEE UNIVERSITY, Gyeonggi-do (KR)

(72) Inventors: Hocheol Kim, Seoul (KR); Jungbin Song, Seoul (KR); Jin Gyu Choi, Seoul (KR)

(73) Assignee: UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 600 days.

(21) Appl. No.: 15/028,388

(22) PCT Filed: Oct. 8, 2014

(86) PCT No.: PCT/KR2014/009484
§ 371 (c)(1),
(2) Date: Apr. 8, 2016

(87) PCT Pub. No.: WO2015/053561
PCT Pub. Date: Apr. 16, 2015

(65) Prior Publication Data
US 2016/0243181 A1    Aug. 25, 2016

(30) Foreign Application Priority Data
Oct. 8, 2013 (KR) .................. 10-2013-0119726

(51) Int. Cl.
*A61K 36/53*   (2006.01)
*A61K 36/00*   (2006.01)
*A61K 36/539*  (2006.01)
*A61K 36/488*  (2006.01)
*A23L 33/105*  (2016.01)

(52) U.S. Cl.
CPC .......... *A61K 36/539* (2013.01); *A23L 33/105* (2016.08); *A61K 36/488* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 7,648,718 B2* | 1/2010 | Kim | A61K 36/254 424/728 |
| 8,017,147 B2* | 9/2011 | Mazed | A61K 36/02 424/450 |
| 9,040,102 B2 | 5/2015 | Yang et al. | 424/741 |
| 2004/0253647 A1* | 12/2004 | Mathews | A61P 25/16 435/7.2 |
| 2008/0241084 A1* | 10/2008 | Siddiqui | A61K 8/97 424/62 |
| 2011/0318435 A1 | 12/2011 | Yang et al. | 424/741 |

FOREIGN PATENT DOCUMENTS

| | | | |
|---|---|---|---|
| CN | 1097552 A | * | 1/1995 |
| CN | 101040928 A | | 9/2007 |
| CN | 102335352 A | * | 2/2012 |
| CN | 102380045 A | * | 3/2012 |
| CN | 103127286 A | * | 6/2013 |
| CN | 103169786 A | * | 6/2013 |
| KR | 10-2003-0007111 | | 1/2003 |
| KR | 10-2007-0002279 | | 1/2007 |
| KR | 2010022128 A | * | 3/2010 |
| KR | 10-2011-0140015 | | 12/2011 |
| WO | WO 2006/080590 | | 8/2006 |

OTHER PUBLICATIONS

Vickers (A Vaccine Against Alzheimer's Disease, Drug Aging 2002: 19(2) 487-494) (Year: 2002).*
Letter/Written Disclosure of the Supplemental Information Disclosure Statement for the above-referenced application, filed herewith on Apr. 6, 2017, 2 pages.
Choi et al., "Phenolic Compounds from *Peuraria lobata* Protect PC12 Cells against Aβ-induced Toxicity," Arch. Pharm. Res. 33(10):1651-1654 (2010).
Database WPI Week 201104, Thomson Scientific, London, GB: An 2010-L87550 XP002766809, & KR 2010 0022128 A [English abstract], 8 pages.
Dong et al., "Effect of total isoflavones from peuraria lobata on the expressions of preproenkephalin, prodynorphin and D2 dopamine receptor mRNA in PC12 cells induced by MPP+*," Chinese-German Journal of Clinical Oncology 9(1):48-52 (2010).
Gasiorowski et al., "Flavones from Root of *Scutellaria baicalensis Georgi*: Drugs of the Future in Neurodegeneration," CNS & Neurological Disorders—Drug Targets 10:184-191 (2011).

(Continued)

*Primary Examiner* — Michael Barker
*Assistant Examiner* — Randall O Winston
(74) *Attorney, Agent, or Firm* — Potomac Law Group, PLLC

(57) ABSTRACT

A composition, a health functional food or a treatment method of the present invention has a remarkable cranial nerve cell protection effect and simultaneously has a sensorimotor function recovery promotion effect and a body weight increasing effect. Accordingly, the present invention has effects of preventing stroke or neurodegenerative diseases, protecting cranial nerve cell cells over the mid to long term immediately after the onset of disease, promoting the recovery of a sensorimotor function reduced by stroke and neurodegenerative diseases, and increasing a reduced body weight. Therefore, the present invention can be used for effectively preventing, treating or managing stroke and neurodegenerative diseases.

16 Claims, 2 Drawing Sheets

(56) References Cited

OTHER PUBLICATIONS

International Preliminary Report on Patentability, dated Apr. 12, 2016, in connection with International Patent Application No. PCT/KR2014/009484 [English translation and original document in Korean], 12 pages.
Extended European Search Report, dated Feb. 17, 2017, in connection with European Patent Application No. 14852440.8, 9 pages.
Letter/Written Disclosure of the Information Disclosure Statement for the above-referenced application, filed herewith on Jul. 7, 2016, 2 pages.
International Search Report and Written Opinion, dated Jan. 16, 2015, in connection with International Patent Application No. PCT/KR2014/009484 [English Translation], 8 pages.
Flowers, F & Zimmerman, J.J., "Reactive oxygen species in the cellular pathophysiology of shock." New Horiz. 6:169-180 (1998) [abstract] [Retreived from the internet on Oct. 20, 2015] Retreived from <URL:ncbi.nlm.nih.gov/pubmed/?term=Flowers+F%2C+Zimmerman+JJ.+New+Horiz.+6%3A169-180%2C+1998, 1 page.
Jones B.J. et al., "The quantitative measurement of motor incoordination in naive mice using an accelerating rotarod," The Journal of pharmacy and pharmacology 20(4): 302-304 (1968).
Kang et al., "Chronological changes of N-methyl-D-aspartate receptors and excitatory amino acid carrier 1 immunoreactivities in CA1 area and subiculum after transient forebrain ischemia." J. Neurocytol. 30: 945-955 (2001).
Kim H.S., "Histological and Functional Changes after Transplantation of Human Mesenchymal Stem Cell in the Ischemic Rat Model," Kor J Cerebrovascular Surgery 7(1): 61-68 (2005) [English Abstract].
Longa et al., "Reversible middle cerebral artery occlusion without craniectomy in rats." Stroke. 20(1): 84-91 (1989).
Machine English translation of Pub. No. KR 10-2003-0007111 (App. No. 2002-0040184), published Jan. 23, 2003, Korean Intellectual Property Office, 26 pages.
Machine English translation of Pub. No. KR 10-2007-0002279 (App. No. 2005-0057720), published Jan. 5, 2007, Korean Intellectual Property Office, 12 pages.
Sun, A.Y. & Chen, Y.M., "Oxidative stress and neurodegenerative disorders." J. Biomed. Sci. 5: 401-414 (1998).
Won et al., "Immunohistochemical detection of oxidative DNA damage induced by ischemia-reperfusion insults in gerbil hippocampus in vivo." Brain Res. 836: 70-78 (1999).
Inoue et al., "Dementia," Shenyang: Liaoning Science and Technology Publishing House, Jan. 2002, 5 pages (English abstract).
Li et al., "Pharmaceutical Comprehensive Knowledge and Skills," Certification Center for Licenses Pharmacist of China Food and Drug Administration, Mar. 2008, 7 pages, China Medical Science and Technology Press, Beijing, China (English abstract).
"Dictionary of Chinese Medicine," Nanjing University of Chinese Medicine, 2nd Edition, Mar. 2006, 9 pages, Shanghai Science and Technology Press (English abstract).
Cui, M. et al., "Study on Extraction and Purification Technology of Geqin Tablets," *Chinese Traditional Patent Medicine*, 28:1275-1277 (2006), China Academic Journal (CD) Electronic Journals Publishing House Co., Ltd., China.

\* cited by examiner

【FIG.1】
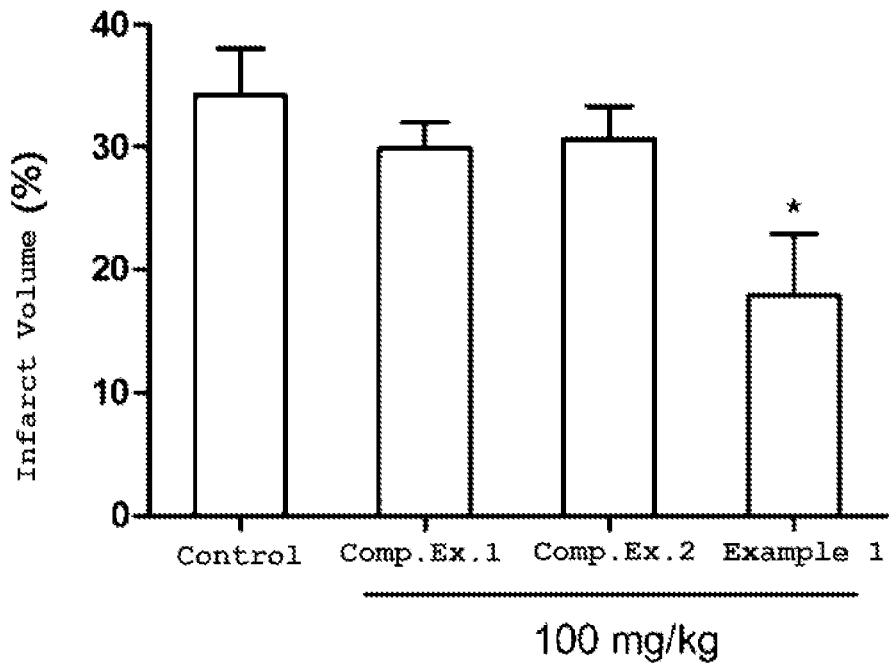
【FIG.2】
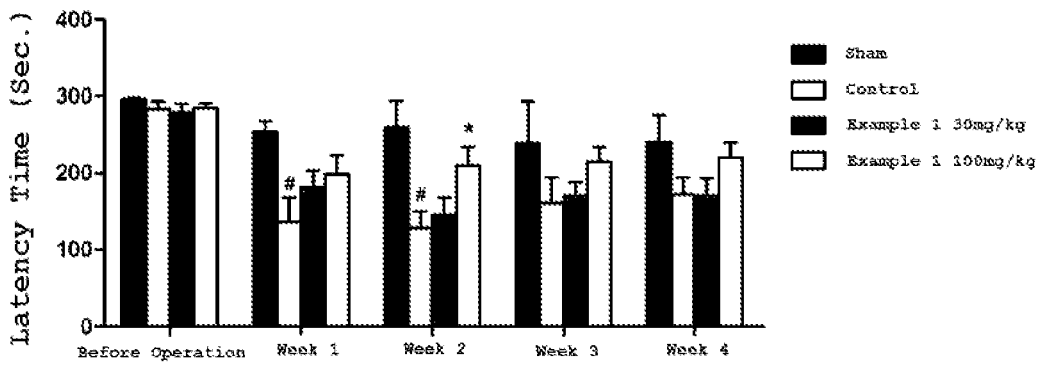
【FIG.3】
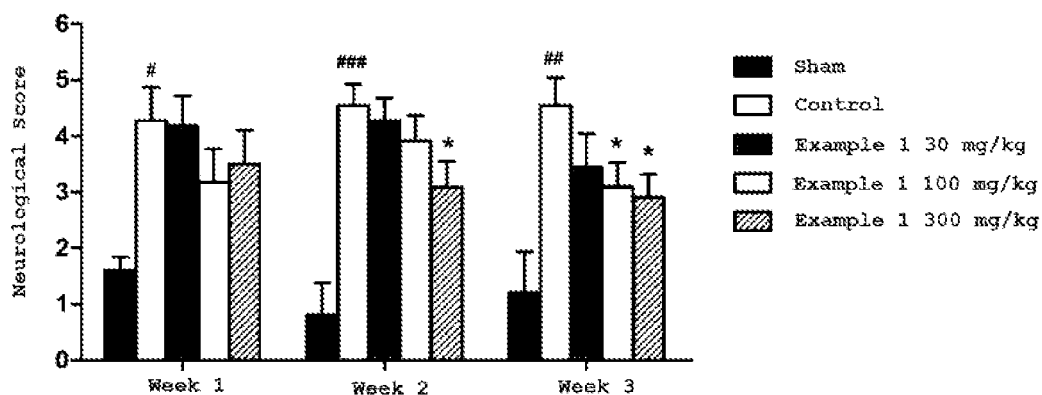

[FIG.4]
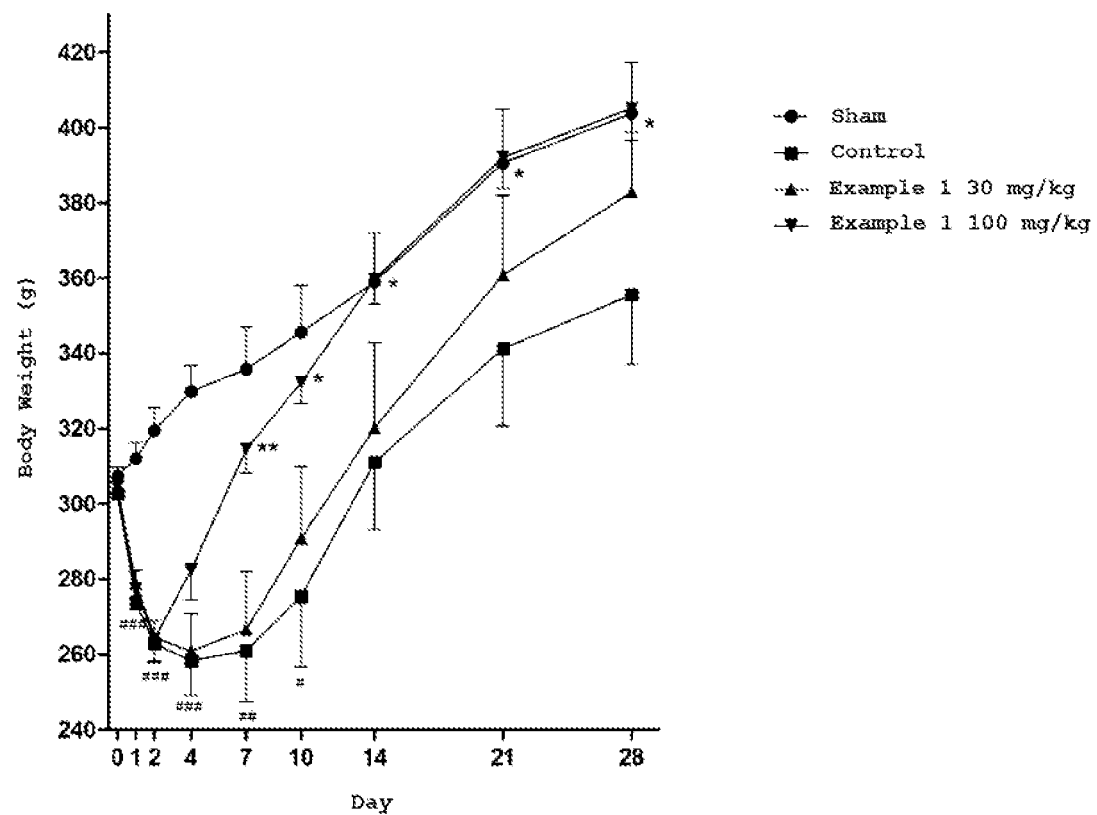

COMPOSITION FOR PREVENTING OR TREATING STROKE OR NEURODEGENERATIVE DISEASE, COMPRISING EXTRACT COMPLEX OF PUERARIA LOBATA AND SCUTELLARIA BAICALENSIS AS ACTIVE INGREDIENT

RELATED APPLICATIONS

This application is the U.S. National Stage of International Application. No. PCT/KR2014/009484, filed 8 Oct. 2014, which claims benefit of priority to Korean Patent Application KR 10-2013-0119726, filed 8 Oct. 2013, the specification of which is incorporated by reference herein.

TECHNICAL FIELD

The present disclosure relates to a pharmaceutical composition and a health functional food for preventing or treating stroke or neurodegenerative diseases.

BACKGROUND

Stroke is sustenance of a rapidly incurred disorder on partial or full function of brain, and there are cerebral infarction (ischemic stroke), which incurs due to cerebrovascular occlusion, and cerebral hemorrhage (hemorrhagic stroke), which incurs when blood leaks into brain tissue due to a rupture of blood vessel of the brain. According to statistics from the American Heart Association (AHA) and American Stroke Association (ASA), ischemic stroke accounts for about 87% of the total stroke globally. Domestically, it increased to 64.7% in 2000 and to 76.1% in 2009 (Clinical Practice Guidelines for Stroke (revised edition, 2013. ISBN 978-89-94181-14-1), Clinical Research Center for Stroke designated by Ministry of Health and Welfare).

Ischemic stroke lead to nerve cell death due to oxygen and nutrition supply cut-off, and accordingly symptoms such as paralysis, language disorder, sensory disturbance, memory impairment and the like incurs because of disorder or loss of function, which the nerve cells are responsible for before apoptosis. The most common symptom of apoplexy is motor disturbance such as weakening of muscle and quadriplegia on impaired side.

So far, the only FDA-approved medicament for ischemic stroke is a tissue plasminogen activator (t-PA), which is a thrombolytic agent. However, t-PA should be administered within 3 hours from onset of apoplexy and thus only a few patients can get administered while most of the patients cannot get administered because of delayed arrival and risk of aggravation of cerebral hemorrhage.

Neurodegenerative diseases include all diseases in which the number of brain nerve cells decreases, and cognitive and sensorimotor impairment incur. Dementia, Alzheimer's disease, Parkinson's disease, Huntington's disease, Pick's disease and Creutzfeld-Jacob disease and the like are types of the neurodegenerative disease. The above-mentioned diseases incur due to various causes and mechanisms but commonly show decrease of brain cells, and cognitive and sensorimotor impairment.

SUMMARY

Technical Problem

The present disclosure provides a pharmaceutical composition and a health functional food for preventing or treating stroke or neurodegenerative diseases having a cranial nerve cell protection effect, a sensorimotor function recovery promotion effect and a body weight increasing effect simultaneously.

Technical Solution

The present disclosure provides the pharmaceutical composition for preventing or treating stroke or neurodegenerative diseases comprising an extract complex of *Pueraria lobata* and *Scutellaria baicalensis* as an active ingredient.

*Pueraria lobata* (Willd.) Ohwi is a perennial climber and belongs in Leguminosae, and its root (Puerariae Radix) is used in Korean and Chinese herbal medicine. *Scutellaria baicalensis* is a perennial herb and belongs in Labiatae, and its root (Scutellariae Radix) is used in Korean and Chinese herbal medicine.

In some embodiment of the present disclosure, the extract complex of *Pueraria lobata* and *Scutellaria baicalensis* can be extracted from a mixture wherein *Pueraria lobata* and *Scutellaria baicalensis* are contained as weight ratio of 100:1 to 1:100. Preferably, the extract complex of *Pueraria lobata* and *Scutellaria baicalensis* can be extracted from a mixture containing 65-95 wt % of *Pueraria lobata* and 5-35 wt % of *Scutellaria baicalensis*, and more preferably the extract complex of *Pueraria lobata* and *Scutellaria baicalensis* can be extracted from a mixture containing 87.91 wt % of *Pueraria lobata* and 12.09 wt % of *Scutellaria baicalensis*. The composition ratios are result of a research conducted by the present inventors for studying the composition ratio which would have superior cranial nerve cell protection effect, a sensorimotor function recovery promotion effect and a body weight increasing effect.

The stroke includes both ischemic stroke and hemorrhagic stroke and preferably, the stroke is directed to ischemic stroke.

The neurodegenerative diseases can be at least one selected from a group consisting of dementia, Alzheimer's disease, Parkinson's disease, Huntington's disease, Pick's disease and Creutzfeld-Jacob disease. However, types of the neurodegenerative diseases are not limited to the above. The neurodegenerative diseases include any disease that can be benefited by the composition of the present disclosure.

The present disclosure provides a composition comprising the extract complex of *Pueraria lobata* and *Scutellaria baicalensis* as an active ingredient for protecting cranial nerve cell and promoting sensorimotor function recovery.

The present disclosure provides a composition comprising the extract complex of *Pueraria lobata* and *Scutellaria baicalensis* as an active ingredient for protecting cranial nerve cell, promoting sensorimotor function recovery and increasing body weight. Patients having stroke and neurodegenerative diseases often display weight loss. For instance, patients having stroke tend to lose their weight rapidly because of insufficient oral nutrition supply due to dysphagia, and it has been reported that weight loss after stroke adversely affects the patients and delays their rehabilitation. The extract complex of *Pueraria lobata* and *Scutellaria baicalensis* of the present disclosure has an effect of increasing the body weight that was reduced by stroke, and thus it can be useful for rehabilitation of patients having stroke and neurodegenerative diseases.

The composition of the present disclosure has a cranial nerve cell protection effect and accordingly, it can prevent or have treating effect on stroke and neurodegenerative diseases immediately after onset of those diseases. Also, the composition has effects of promoting the recovery of a sensorimotor function reduced by stroke and neurodegenerative diseases and increasing a reduced body weight over the mid to long term. Therefore, the present disclosure can be used for effectively preventing, treating or managing stroke and neurodegenerative diseases.

The pharmaceutical composition of the present disclosure comprises the extract complex of *Pueraria lobata* and *Scutellaria baicalensis* as an active ingredient, and an adequate ratio of the active ingredient can be determined based on the purpose of use (i.e. prevention or medical treatment). Generally, the extract complex of *Pueraria lobata* and *Scutellaria baicalensis* can be added in the ratio of 0.0001 wt % to 100 wt % based on total weight of the composition.

The composition of the present disclosure can be administered orally or parenterally. Preferably, it can be a parenteral administration, and more preferably, it can be an intravenous administration. When formulating, common diluents such as fillers, extenders, binders, humectants, disintegrants, surfactants and the like or excipients can be used.

Formulations for parenteral administration include sterile aqueous solutions, nonaqueous solvents, suspensions, emulsions, lyophilized formulations and suppositories. Injectable esters such as propylene glycol, polyethylene glycol, vegetable oils and ethyl oleate can be used as the nonaqueous solvents and suspensions. Witepsol, macrogol, tween 61, cacao butter, laurinum, glycerol and gelatin can be used as base material of the suppositories. The pharmaceutical composition of the present disclosure can be administered parenterally by subcutaneous, venous or intramuscular injection.

The dosage of the pharmaceutical composition of the present disclosure may vary depending on patients' status, body weight, disease progression, form of drug, and route and duration of administration. It can be properly selected by those skilled in the art. However, to achieve a desirable effect, the composition of the present disclosure can be administered in a dosage of 0.0001 to 2,000 mg/kg per a day and preferably, 0.1 to 1,000 mg/kg per a day. Administration can be made once a day or divided into several times per a day. However, the said dosage explained hereinbefore does not limit scope of the present disclosure.

The composition of the present disclosure can be used solely or jointly with an operation, hormone therapy, chemotherapy and biological response modifier therapies for preventing or treating stroke or neurodegenerative diseases.

The present disclosure provides a health functional food comprising the extract complex of *Pueraria lobata* and *Scutellaria baicalensis* as an active ingredient for preventing or improving stroke or neurodegenerative diseases.

In some embodiment of the present disclosure, the extract complex of *Pueraria lobata* and *Scutellaria baicalensis* can be extracted from the mixture wherein *Pueraria lobata* and *Scutellaria baicalensis* are contained as weight ratio of 100:1 to 1:100. Preferably, the extract complex of *Pueraria lobata* and *Scutellaria baicalensis* can be extracted from the mixture containing 65-95 wt % of *Pueraria lobata* and 5-35 wt % of *Scutellaria baicalensis*, and more preferably the extract complex of *Pueraria lobata* and *Scutellaria baicalensis* can be extracted from the mixture containing 87.91 wt % of *Pueraria lobata* and 12.09 wt % of *Scutellaria baicalensis*.

The present disclosure provides a health functional food comprising the extract complex of *Pueraria lobata* and *Scutellaria baicalensis* as an active ingredient for protecting cranial nerve cell, promoting sensorimotor function recovery and increasing body weight.

It is preferable to prepare the extract complex of *Pueraria lobata* and *Scutellaria baicalensis* of the present disclosure by a method comprising following steps, but not limited to it:

(1) removing foreign objects from *Pueraria lobata* and *Scutellaria baicalensis*, washing and comminuting the same;
(2) adding an extraction solvent to the mixture of washed and comminuted *Pueraria lobata* and *Scutellaria baicalensis*, and extracting the same;
(3) concentrating the extract under reduced pressure;
(4) filtering the concentrate; and
(5) drying the filtered extract.

It is preferable to repeat the washing in step (1) 1-5 times.

The extraction in step (2) can be shaking extraction, soxhlet extraction or reflux extraction but not limited to these. The extraction solvent can be water, $C_{1-4}$ alcohol or mixtures thereof. It is most preferable to perform a hot water extraction by using ethanol. It is preferable to extract with addition of 3 to 10 times of the extraction solvent based on total weight of the prepared *Pueraria lobata* and *Scutellaria baicalensis*.

The hot water extraction can be performed by pressurizing. The pressure is preferably 1.1-2.0 atm, and more preferably 1.2-1.5 atm.

Additionally, it is preferable for the hot water extraction to use the water at 60-100° C., and more preferably 80-90° C. Also, it is preferable for extraction duration to be 2-24 hours, and extraction to be repeated 1-5 times.

It is preferable to use a vacuum evaporator or a rotary vacuum evaporator for the concentration in step (3). It is preferable to concentrate the extracts of step (3) to have more than 40% of solid content.

The drying in step (5) can be drying under reduced pressure, drying in vacuo, boiling-drying, spray-drying or freeze-drying but not limited to these.

The health functional food of the present disclosure comprises the extract complex of *Pueraria lobata* and *Scutellaria baicalensis* as an active ingredient, and adequate ratio of the active ingredient can be determined based on the purpose of use (i.e. prevention, improvement or medical treatment). Generally, the extract complex of *Pueraria lobata* and *Scutellaria baicalensis* can be added in the ratio of 0.0001 wt % to 100 wt % based on total weight of the health functional food.

In addition, there are no specific limitations on types of the health functional food. The present disclosure can be applied as beverage, gum, vitamin complex, drink preparation and the like. It includes all kind of conventional health functional foods.

When preparing the health functional food of the present disclosure in a form of beverage, various flavoring agents or natural carbohydrates and the like can be additionally comprised therein as conventional beverages. The natural carbohydrate can be sugars including monosaccharide such as glucose, fructose and the like; disaccharide such as maltose, sucrose and the like; polysaccharide such as dextrin, cyclodextrin and the like; and sugar alcohols such as xylitol, sorbitol, erythritol and the like. Other flavoring agents such as saccharin, aspartame and the like can also be used.

The health functional food of the present disclosure can comprise various nutritional supplements, vitamins, minerals (electrolytes), flavoring agents including synthetic flavoring agents and natural flavoring agents, coloring agents and enhancers (i.e. cheese, chocolate and the like), pectic acid and its salt, alginic acid and its salt, organic acid, protective colloid thickeners, pH modifiers, stabilizers, preservatives, glycerin, alcohol, carbonators for carbonated beverages and the like.

The health functional food of the present disclosure can be used solely or jointly with an operation, hormone therapy, chemotherapy and biological response modifier therapies for preventing or treating stroke or neurodegenerative diseases.

The present disclosure provides a method of preventing, improving or treating stroke or neurodegenerative diseases by administering therapeutically effective amount of the extract complex of *Pueraria lobata* and *Scutellaria baicalensis* to subjects in need of treatment.

The present disclosure provides a method of protecting cranial nerve cell, promoting sensorimotor function recovery and increasing body weight by administering therapeutically effective amount of the extract complex of *Pueraria lobata* and *Scutellaria baicalensis* to subjects in need of treatment.

In some embodiment of the present disclosure, the extract complex of *Pueraria lobata* and *Scutellaria baicalensis* can be extracted from the mixture wherein *Pueraria lobata* and *Scutellaria baicalensis* are contained as weight ratio of 100:1 to 1:100. Preferably, the extract complex of *Pueraria lobata* and *Scutellaria baicalensis* can be extracted from the mixture containing 65-95 wt % of *Pueraria lobata* and 5-35 wt % of *Scutellaria baicalensis*, and more preferably the extract complex of *Pueraria lobata* and *Scutellaria baicalensis* can be extracted from the mixture containing 87.91 wt % of *Pueraria lobata* and 12.09 wt % of *Scutellaria baicalensis*.

The term 'subjects in need of treatment' is directed to mammals including human being, and the term 'administration' is directed to provision of desired substances to patients through any proper methods. The term 'therapeutically effective amount' is directed to an amount of active ingredient or pharmaceutical composition that induces biological or medical responses from animals or human beings, which are considered as so by researchers, veterinarians, doctors or other clinicians. It includes an amount wherethrough alleviation of symptoms of diseases or disorders being treated could be induced. It is obvious to those skilled in the art that the therapeutically effective amount and administration frequency of the active ingredients of the present disclosure can vary depending on desired effects.

The present disclosure provides a use of the extract complex of *Pueraria lobata* and *Scutellaria baicalensis* for the manufacture of pharmaceutical formulations for treating stroke or neurodegenerative diseases. The use of the present disclosure can be applied to preparation of pharmaceutical formulations for protecting cranial nerve cell, promoting sensorimotor function recovery and increasing body weight.

In some embodiment of the present disclosure, the extract complex of *Pueraria lobata* and *Scutellaria baicalensis* can be extracted from the mixture wherein *Pueraria lobata* and *Scutellaria baicalensis* are contained as weight ratio of 100:1 to 1:100. Preferably, the extract complex of *Pueraria lobata* and *Scutellaria baicalensis* can be extracted from the mixture containing 65-95 wt % of *Pueraria lobata* and 5-35 wt % of *Scutellaria baicalensis*, and more preferably the extract complex of *Pueraria lobata* and *Scutellaria baicalensis* can be extracted from the mixture containing 87.91 wt % of *Pueraria lobata* and 12.09 wt % of *Scutellaria baicalensis*.

The pharmaceutical composition, the health functional food, the method of treatment and the use for preparation of the pharmaceutical formulations have a cranial nerve cell protection effect on cerebral ischemia, and simultaneously have a remarkable sensorimotor function recovery promotion effect and a body weight increasing effect. In other words, pertaining to the time window for the treatment of stroke due to cerebral ischemia, the above effects also include a cranial nerve cell protection effect that prevents a delayed neuronal death, which occurs for several days after onset of stroke, and simultaneously, effects of recovering sensorimotor function and increasing a body weight after the acute stage of stroke. The effects of promoting sensorimotor function recovery and increasing body weight have different mechanism to that of the cranial nerve cell protection effect, thus a drug simultaneously having these effects has not been developed yet.

The effects of the pharmaceutical composition, the health functional food, the method of treatment and the use for preparation of the pharmaceutical formulations are confirmed through a rat model of middle cerebral artery occlusion. So far, there are two widely known mechanisms for neural death caused by cerebral ischemia. One is an excitatory neural death mechanism (Kang T C, et al., J. Neurocytol., 30:945-955, 2001) in which neural death is induced by an excessive accumulation of calcium in cells due to influx of excessively accumulated glutamate at outside of cells due to cerebral ischemia, and the other is oxidative neural death (Won M H, et al., Brain Res., 836:70-78, 1999; Sub A Y., Chen Y M., J. Biomed. Sci., 5:401-414, 1998; Flowers F, Zimmerman J J. New Horiz. 6:169-180, 1998) in which neural death is induced by damages to DNA and cytoplasm due to increment of in vivo radicals caused by sudden oxygen supply at the time of ischemia-refusion. The animal model is adequate to observe prevention or treatment effect of neuronal death caused by cerebral ischemia because both oxidative neuronal death and excitatory neuronal death occurs in this model.

Advantageous Effect

The composition, the health functional food or the treatment method of the present disclosure has a remarkable cranial nerve cell protection effect and simultaneously has a sensorimotor function recovery promotion effect and a body weight increasing effect. Accordingly, the present disclosure has effects of preventing stroke or neurodegenerative diseases, protecting cranial nerve cell cells over the mid to long term immediately after the onset of disease, promoting the recovery of a sensorimotor function reduced by stroke and neurodegenerative diseases, and increasing a reduced body weight. Therefore, the present disclosure can be used for effectively preventing, treating or managing stroke and neurodegenerative diseases.

BRIEF DESCRIPTION OF DRAWINGS

FIG. 1 is a graph showing infarct volume of rats in a control, a *Pueraria lobata* extract administered group, a *Scutellaria baicalensis* extract administered group and an extract complex of *Pueraria lobata* and *Scutellaria baicalensis* administered group.

FIG. 2 is a graph showing a latency time (time until falls from a rotarod) of a sham-operated group, the control, an extract complex of *Pueraria lobata* and *Scutellaria baicalensis* administered group (30 mg/kg) and an extract complex of *Pueraria lobata* and *Scutellaria baicalensis* administered group (100 mg/kg).

FIG. 3 is a graph showing a neurological score of the sham-operated group, the control, the extract complex of *Pueraria lobata* and *Scutellaria baicalensis* administered group (100 mg/kg) and an extract complex of *Pueraria lobata* and *Scutellaria baicalensis* administered group (300 mg/kg).

FIG. 4 is a graph showing weight variation of the sham-operated group, the control, the extract complex of *Pueraria lobata* and *Scutellaria baicalensis* administered group (30 mg/kg) and the extract complex of *Pueraria lobata* and *Scutellaria baicalensis* administered group (100 mg/kg).

DESCRIPTION OF EMBODIMENTS

The present inventors observed effects of various Chinese herbal medicines on treating stroke or neurodegenerative diseases, and as a result of the observation, the inventors confirmed through the animal MCAo model that the composition comprising the extract complex of *Pueraria lobata* and *Scutellaria baicalensis* as active ingredient has a remarkable cranial nerve cell protection effect on neuronal cell damage due to cerebral ischemia, and simultaneously has a superior sensorimotor function recovery promotion effect and a body weight increasing effect, and accordingly completed the present disclosure.

The present disclosure will be described more fully hereinafter with reference to the accompanying examples. However, the present disclosure may be embodied in many different forms, and should not be construed as being limited to the embodiments set forth herein.

Example 1

Preparation of the Extract Complex of *Pueraria lobata* and *Scutellaria baicalensis*

Root of *Pueraria lobata* (hereinafter referred to "*Pueraria lobata*") and Root of *Scutellaria baicalensis* hereinafter referred to "*Scutellaria baicalensis*") were purchased from Yaksudang herbal shop (Dongdaemun-gu, Seoul). A mixture was prepared by mixing 87.91 g of comminuted *Pueraria lobata* and 12.09 g of comminuted *Scutellaria baicalensis*. 10-fold of 30% ethanol (1 L) was added to the mixture. The mixture was extracted through the primary hot water extraction for 3 hours at 90° C., left for 2-3 hours at room temperature and then filtered. The filtrate therefrom was set as the primary extract. 30% ethanol (1 L) was added into the extractor again and extracted through the secondary hot water extraction for 3 hours at 80-90° C. The extract was left for 2-3 hours at room temperature and filtered. The filtrate therefrom was set as the secondary extract. The primary extract and the secondary extract were mixed and concentrated under reduced pressure at 50-60° C. until it reaches to 20 brix. The resulting concentrate was pre-freezed for 20 minutes at −45° C. by using a pre-freezer, and lyophilized by using a freeze drier to prepare powdered concentrate.

Comparative Example 1

Preparation of the *Pueraria lobata* Extract

The *Pueraria lobata* extract was prepared by extracting 100 g of *Pueraria lobata* in the same manner as Example 1.

Comparative Example 2

Preparation of the *Scutellaria baicalensis* Extract

The *Scutellaria baicalensis* extract was prepared by extracting 100 g of *Scutellaria baicalensis* in the same manner as Example 1.

The contents of the *Pueraria lobata* extract and the *Scutellaria baicalensis* extract in Example 1 and Comparative Examples 1 and 2 were described in Table 1 below.

TABLE 1

| | | *Pueraria lobata* | *Scutellaria baicalensis* |
|---|---|---|---|
| Example 1 | Weight (g) | 87.91 | 12.09 |
| | Weight Ratio | 8 | 1.1 |
| Comparative Example 1 | Weight (g) | 100 | 0 |
| | Weight Ratio | 1 | 0 |
| Comparative Example 2 | Weight (g) | 0 | 100 |
| | Weight Ratio | 0 | 1 |

Experimental Example 1

Preparation of the Animal Model

<1-1> Preparation of a Experiment Animal

Male 8-week-old Sprague-Dawley rats in about 300 g (Samtako Inc., Republic of Korea) were housed and received enough feed and water to adapt to the experimental environment. About 1 week was given to the rats for adaptation, and then the animal experimentation was performed.

<1-2> Preparation of the Animal Model

Local cerebral ischemia was induced by applying the method of Zea Longa et al. (Longa E Z, Weinstein P R, Carlson S, Cummins R. Reversible middle cerebral artery occlusion without craniectomy in rats. Stroke; a journal of cerebral circulation. 1989; 20(1): 84-91). The rats prepared in Experimental Example <1-1> were put under general anesthesia by using mixed gas (70% $N_2O$ and 30% $O_2$) and 5% isoflurane, and then left carotid artery and external carotid artery (ECA) were separated from surrounding tissue and nerve by incising central-front skin of neck. Superior thyroid artery and laryngeal artery (i.e. branches of external carotid artery), and pterygopalatine artery (i.e. branch of internal carotid artery) were electro-cauterized. External carotid artery was incised and a probe (Doccol, Redlands, Calif., USA) was inserted into internal carotid artery through external carotid artery, but the probe was inserted about 18-19 mm from common carotid artery branch and fixed with a thread. Incised skin was resutured and the rats were allowed to rest for spontaneous recovery from anesthesia. The rats were anesthetized again after 60 minutes of induction in the same way and reperfusion was by pulling back the probe. All operation procedures were conducted beneath an operating microscope while maintaining the isofluran at 2%, and a device for the maintenance of body temperature was used to maintained the body temperature not to drop below 37±0.5° C.

Example 2

Comparison of Cranial Nerve Cell Protection Effects of Example 1 and Comparative Examples 1-2 by Using Animal Model Middle cerebral artery occlusion was induced to the rat for 90 minutes in the same manner as <Experimental Example 1>. The rats were divided into 4 groups. Each 100 mg/kg of a vehicle (5% DMSO) for the first group, the *Pueraria lobata* extract of Comparative Example 1 for the second group, the *Scutellaria baicalensis* extract of Comparative Example 2 for the third group, and the extract complex of *Pueraria lobata* and *Scutellaria baicalensis* of Example 1 for the fourth group were orally administered once right after the induction. The rats were sacrificed for humane reasons after 24 hours from the reperfusion and the brain was recovered within 2 minutes. The recovered brain was sliced into 6 sections at a thickness of 2 mm by using a rat brain matrix. The brain sections were dipped in a 12 well plate containing 2% 2,3,5-triphenyltetrazolium chloride (TTC) solution and stained for 30 minutes at 37° C. The stained brain sections were photographed by using a digital camera, and then infarct volume was measured by using Image Pro plus 5.0, which is image analysis software. Infarct volume (%) was calculated by the formula below.

Infract Volume (%)=(A−B/A)×100

A: volume of normal left hemisphere (mm$^3$)
B: volume of damaged cerebral infarct area (mm$^3$)

Infract volume of the extract complex of *Pueraria lobata* and *Scutellaria baicalensis* administered group was significantly decreased by 47.9% compared to that of the control ($p<0.05$). However, the *Pueraria lobata* administered group and the *Scutellaria baicalensis* administered group exhibited no statistically significant effect compared to the control (FIG. 1). The result of the above experimentation was described in Table 2 below.

TABLE 2

|  | Infract Volume (%) | Decrease Ratio (%) |
| --- | --- | --- |
| Control | 34.2 ± 3.8 |  |
| Comparative Example 2 | 30.7 ± 2.6 | 10.4 |
| Comparative Example 1 | 29.9 ± 2.2 | 12.7 |
| Example 1 | 17.8 ± 5.1 | 47.9* |

*P < 0.05

Example 3

Observation of Function Recovery Promotion Effect of the Extract Complex on Sensorimotor Function Impairment by Using the Animal Model Middle cerebral artery occlusion was induced to the rats for 60 minutes in the same manner as <Experimental Example 1>. The rats were divided into 4 groups as the sham-operated group, the control, the extract complex of *Pueraria lobata* and *Scutellaria baicalensis* of Example 1 administered group (30 mg/kg) and the extract complex of *Pueraria lobata* and *Scutellaria baicalensis* of Example 1 administered group (100 mg/kg). Three days after the operation, the extract complex at the volume of 5 ml/kg was orally administered to the extract complex administered groups or in case of the sham-operated group and the control, the vehicle (5% DMSO) at the volume of 5 ml/kg was orally administered once a day for 14 days.

To evaluate rats' motor coordination and balance alteration, a rotarod test was conducted one day before the operation and 1, 2, 3 and 4 weeks after the operation by applying the method of Jones B J et al. (Jones B J, Roberts D J. The quantitative measurement of motor incoordination in naive mice using an accelerating rotarod. The Journal of pharmacy and pharmacology. 1968; 20(4): 302-4). An accelerating version of the rotarod, wherein the rotating rod (B1001, B.S Technolab INC., Republic of Korea) is rotating for 5 minutes from 5 to 30 rpm, was used. The rat was placed on the middle of the rod while keeping its balance and latency time was measured at which the rat falls off the rod. The test was performed 5 times per each rat. The highest and lowest values were discarded and the remaining three were averaged.

The rotarod test was conducted on one day before the operation and 1, 2, 3 and 4 weeks after the operation to observe effect of the extract complex on improving sensorimotor function impairment, and the result therefrom was illustrated in FIG. 2. As a result of measuring the latency time of every group before the operation, the sham-operated group, the control, the extract complex of *Pueraria lobata* and *Scutellaria baicalensis* administered group (30 mg/kg) and the extract complex of *Pueraria lobata* and *Scutellaria baicalensis* administered group (100 mg/kg) showed latency time of 296.0±2.6, 283.9±9.7, 278.9±11.7, 284.4±6.6 seconds respectively. It was confirmed that there were no difference among every group. In case of the control, the latency time was rapidly decreased compared to that of the sham-operated group (137.2±30.3 vs. 253.8±13.8 sec, $p<0.05$) when measuring the latency time one week after the middle cerebral artery occlusion operation. However, latency time of the groups wherein the extract complex of *Pueraria lobata* and *Scutellaria baicalensis* was administered was comparatively longer than that of the control. After 2 weeks, the extract complex of *Pueraria lobata* and *Scutellaria baicalensis* administered group and the control were compared and it was confirmed that latency time of the extract complex of *Pueraria lobata* and *Scutellaria baicalensis* administered group was 1.6 times increased compared to that of the control (210.2±23.6 vs. 129.3±20.8 sec, $p<0.05$).

Example 4

Observation of Recovery Promotion Effect of the Extract Complex on Neurological Damage The rats were divided into 5 groups as the sham-operated group, the control, the extract complex of *Pueraria lobata* and *Scutellaria baicalensis* administered group (30 mg/kg), the extract complex of *Pueraria lobata* and *Scutellaria baicalensis* administered group (100 mg/kg) and the extract complex of *Pueraria lobata* and *Scutellaria baicalensis* administered group (300 mg/kg), and middle cerebral artery occlusion was induced to the rats for 60 minutes in the same manner as <Experimental Example 1>. From 4 days after the operation, the extract complex at the volume of 5 ml/kg was orally administered to the groups once a day for 14 days. In case of the sham-operated group and the control, the vehicle (5% DMSO) was administered in the same manner as the extract complex administered groups.

A mNSS (modified Neurological Severity Score) test was conducted on 7$^{th}$, 14$^{th}$ and 21$^{th}$ day of the operation to evaluate neurological function by applying the method of H S Kim et al. (Kim H S. Histological and Functional Changes after Transplantation of Human Mesenchymal Stem Cell in the Ischemic Rat Model. Kor J Cerebrovascular Surgery. 2005; 7(1): 61-8). Higher scores correspond to severer dysfunction, 0 means normal and 7 is the highest neurological score.

The result of mNSS test conducted on 1, 2 and 3 weeks after the operation is illustrated in FIG. 3. The mNSS score of the control measured 1 week after the cerebral ischemia induction was significantly increased compared to that of the sham-operated group (4.3±0.6 vs. 1.6±0.2, $p<0.05$). The mNSS score of the extract complex of *Pueraria lobata* and Scutellaria baicalensis administered group (300 mg/kg) measured 2 weeks after the cerebral ischemia induction was 3.1±0.5 and it was significantly decreased score compared to 4.5±0.4, which was the score of the control (p<0.05). The mNSS score of the extract complex of *Pueraria lobata* and *Scutellaria baicalensis* administered groups (100 mg/kg and 300 mg/kg) measured 3 weeks after the cerebral ischemia induction were 3.1±0.4 and 2.9±0.4 respectively and it was confirmed that these were significantly decreased scores compared to 4.5±0.5, which was the score of the control (in every case, p<0.05).

Example 5

Observation of Improving Effect of the Extract Complex on Weight Loss

The rats were divided into 4 groups as the sham-operated group, the control, the extract complex of *Pueraria lobata* and *Scutellaria baicalensis* administered group (30 mg/kg) and the extract complex of *Pueraria lobata* and *Scutellaria baicalensis* administered group (100 mg/kg), and middle cerebral artery occlusion was induced to the rat for 60 minutes in the same manner as <Experimental Example 1>. From 3 days after the operation, the extract complex at the volume of 5 ml/kg was orally administered to the groups once a day for 14 days. In case of the sham-operated group and the control, the vehicle (5% DMSO) was administered in the same manner as the extract complex administered groups.

Body weights were measured at the same time everyday from the initial date of the operation until the end of the experimentation, which was 28 days after the operation.

The body weight variation of each group measured from the initial date of the operation until the end of the experimentation was illustrated in FIG. 4. The body weight measured right before the operation ($0^{th}$ day) among groups were not significantly different. After the operation, body weights of the control were rapidly decreased. It was 258.3±9.0 g at the $4^{th}$ day, which was 14.7% decreased weight compared to the initial weight 302.7±1.2 g. There was a significant difference in body weights between the sham-operated group and the control until $10^{th}$ day. Body weights of the extract complex of *Pueraria lobata* and *Scutellaria baicalensis* administered group (100 mg/kg) began to increase after the administration and showed significant difference compared to that of the control since the $7^{th}$ day to the $28^{th}$ day, when the experimentation was ended. Specifically, at the $14^{th}$ day of the induction, the body weight of the extract complex of *Pueraria lobata* and *Scutellaria baicalensis* administered group (100 mg/kg) was 359.8±6.7 g, which was almost similar to the body weight of the sham-operated group (359.0±13.0 g).

INDUSTRIAL APPLICABILITY

The present disclosure can effectively prevent, treat or improve stroke or neurodegenerative diseases.

The invention claimed is:

1. A method for treating a cerebral ischemia or ischemic stroke in subject comprising administering to the subject an effective amount of a pharmaceutical composition comprising an extract complex of *Pueraria lobate* and *Scutellaria baicalensis* as an active ingredient, wherein the extract complex of *Pueraria lobata* and *Scutellaria baicalensis* is extracted from a mixture containing 65-95 wt % of *Pueraria lobata* and 5-35 wt % of *Scutellaria baicalensis*.

2. The method according to 1, wherein the extract complex of *Pueraria lobata* and *Scutellaria baicalensis* is extracted from a mixture containing 87.91 wt % of *Pueraria lobata* and 12.09 wt % of *Scutellaria baicalensis*.

3. A method for treating a cerebral ischemia or ischemic stroke in subject comprising administering to the subject an effective amount of a health functional food comprising the extract complex of *Pueraria* lobate and *Scutellaria baicalensis* as an active ingredient, wherein the extract complex of *Pueraria lobata* and *Scutellaria baicalensis* is extracted from a mixture containing 65-95 wt % of *Pueraria lobata* and 5-35 wt % of *Scutellaria baicalensis*.

4. The method according to 3, wherein the extract complex of *Pueraria lobata* and *Scutellaria baicalensis* is extracted from the mixture containing 87.91 wt % of *Pueraria lobata* and 12.09 wt % of *Scutellaria baicalensis*.

5. The method according to 1, wherein the composition is for protecting neuron and promoting sensorimotor function recovery.

6. The method according to 1, wherein the composition is for increasing body weight.

7. The method according to 3, wherein the health functional food is for protecting neuron and promoting sensorimotor function recovery.

8. The method according to 3, wherein the health functional food is for increasing body weight.

9. A method for treating stroke in subject comprising administering to the subject an effective amount of a pharmaceutical composition comprising an extract complex of *Pueraria* lobate and *Scutellaria baicalensis* as an active ingredient, wherein the extract complex of *Pueraria lobata* and *Scutellaria baicalensis* is extracted from a mixture containing 65-95 wt % of *Pueraria lobata* and 5-35 wt % of *Scutellaria baicalensis*.

10. The method according to 9, wherein the extract complex of *Pueraria lobata* and *Scutellaria baicalensis* is extracted from a mixture containing 87.91 wt % of *Pueraria lobata* and 12.09 wt % of *Scutellaria baicalensis*.

11. A method for treating stroke in subject comprising administering to the subject an effective amount of a health functional food comprising the extract complex of *Pueraria* lobate and *Scutellaria baicalensis* as an active ingredient, wherein the extract complex of *Pueraria lobata* and *Scutellaria baicalensis* is extracted from a mixture containing 65-95 wt % of *Pueraria lobata* and 5-35 wt % of *Scutellaria baicalensis*.

12. The method according to 11, wherein the extract complex of *Pueraria lobata* and *Scutellaria baicalensis* is extracted from the mixture containing 87.91 wt % of *Pueraria lobata* and 12.09 wt % of *Scutellaria baicalensis*.

13. The method according to 9, wherein the composition is for protecting neuron and promoting sensorimotor function recovery.

14. The method according to 9, wherein the composition is for increasing body weight.

15. The method according to 11, wherein the health functional food is for protecting neuron and promoting sensorimotor function recovery.

16. The method according to 11, wherein the health functional food is for increasing body weight.

* * * * *